(12) United States Patent
Hua et al.

(10) Patent No.: US 8,992,990 B2
(45) Date of Patent: *Mar. 31, 2015

(54) MAGNETIC NANOCOMPOSITE FOR INHIBITING/TREATING CANCER AND METHOD FOR FABRICATING THE SAME

(75) Inventors: Mu-Yi Hua, Tao-Yuan (TW); Hung-Wei Yang, Tao-Yuan (TW); Rung-Ywan Tsai, Kaohsiung (TW); Kuo-Chen Wei, Taipei (TW); Pin-Yuan Chen, Taipei (TW); Chiung-Yin Huang, Yangmei Township, Taoyuan County (TW)

(73) Assignee: Chang Gung University, Kwei-Shan, Tao-Yuan (TW)

( * ) Notice: Subject to any disclaimer, the term of this patent is extended or adjusted under 35 U.S.C. 154(b) by 284 days.

This patent is subject to a terminal disclaimer.

(21) Appl. No.: 12/799,887

(22) Filed: May 4, 2010

(65) Prior Publication Data

US 2011/0104294 A1    May 5, 2011

(30) Foreign Application Priority Data

Nov. 2, 2009  (TW) ................ 98137256 A (51) Int. Cl.
  *A61K 47/48*    (2006.01)
  *A01N 47/34*    (2006.01)
  *A61K 31/17*    (2006.01)

(52) U.S. Cl.
  CPC .............. *A61K 47/48861* (2013.01)
  USPC ....................................... 424/497

(58) Field of Classification Search
  USPC ....................................... 514/769
  See application file for complete search history.

(56) References Cited

U.S. PATENT DOCUMENTS 5,237,023 A * 8/1993 Oka ............................. 525/540
2006/0177379 A1 * 8/2006 Asgari ......................... 424/9.3

OTHER PUBLICATIONS

Xie et al., "Iron Oxide Nanoparticle Platform for Biomedical Applications", Apr. 2009, Current Medicinal Chemistry, vol. 16, No. 10, pp. 1278-1294.*
Yang et al., "A new drug of BCNU bound on magnetic nano-particles and their in vitro antitumor activity against Glioma C6 cells," 2009 IEEE International Magnetics Conference, May 4-8, 2009.

* cited by examiner

*Primary Examiner* — Michael B Pallay
(74) *Attorney, Agent, or Firm* — Muncy, Geissler, Olds & Lowe, P.C.

(57) ABSTRACT

The present invention discloses a magnetic nanocomposite for inhibiting/treating cancer and a method for fabricating the same. The magnetic nanocomposite comprises a core formed of a plurality of magnetic nanoparticles made of ferric ferrous oxide ($Fe_3O_4$); a shell made of a carboxy-functionalized polyaniline; and an anti-tumor medicine bound to the external surface of the shell. The method of the present invention fast fabricates the magnetic nanocomposite in a simple way. The medicine of the present invention has a longer half life and a better thermal stability. The present invention disperses the water-insoluble medicine in water uniformly to decrease the biological rejection. Moreover, the magnetic nanocomposite of the present invention is guided to the nidus by an external magnetic field to increase the local concentration of the medicine and provide an effective chemotherapy. Therefore, the present invention has competitive advantage over the conventional BCNU.

12 Claims, 12 Drawing Sheets

(12 of 12 Drawing Sheet(s) Filed in Color)

MAGNETIC NANOCOMPOSITE FOR INHIBITING/TREATING CANCER AND METHOD FOR FABRICATING THE SAME

BACKGROUND OF THE INVENTION

1. Field of the Invention

The present invention relates to a medicine vector and a method for fabricating the same, particularly to a magnetic nanocomposite for inhibiting/treating cancer and a method for fabricating the same.

2. Description of the Related Art

The current vector technologies for anti-cancer medicine may be categorized into the following three types.

(1) Liposome packages an anti-cancer medicine and a particle. The technology can protect the medicine from being dissolved by enzyme and thus can gradually release medicine. However, the technology cannot control the release speed and release quantity of medicine. Further, the vectors cannot be concentrated on a special region but are distributed all over the body. Therefore, the anti-cancer medicine would cause a general damage to the patient. Furthermore, the particle size used in the technology is too great (about 200-600 nm) to be intravenously injected into the body. Moreover, the quantity of the anti-cancer medicine enveloped by liposome is influenced by particle size, and the medicine release rate is thus hard to control.

(2) A semiconductor device functions as the vector of anti-cancer medicine. The semiconductor device wrapping anti-cancer medicine is implanted into a cancer to directly release the anti-cancer medicine to the cancer. The technology can increase the local concentration of the medicine to apply an intensified therapy to the nidus. Thus, the technology can exempt the patient from the general side effect caused by the anticancer medicine. However, the patient must risk a surgical operation for implanting the vector into the body.

(3) A biocompatible and biodegradable polymer and an anti-cancer medicine are mixed to fabricate a complex medicine. Similar to the liposome package technology, the technology can gradually release medicine and prolong the retention time of medicine. Similar to the liposome package technology, the technology neither concentrates medicine on the nidus nor exempts healthy tissues from being damaged by anti-cancer medicine.

SUMMARY OF THE INVENTION

The conventional medicine vector can prevent from rapid decomposition of medicine and facilitate gradual release of medicine. However, the medicine release rate is limited by the vector size and hard to control. The primary objective of the present invention is to provide a magnetic nanocomposite for inhibiting/treating cancer and a method for fabricating the same, wherein a simple process is used to fast fabricate a biocompatible magnetic nanocomposite that can promote the thermal stability of medicine and decrease the in-vivo hydrolysis rate of medicine, and wherein the magnetic nanocomposite can carry medicine to the cancered region via the guiding of an external magnetic field, whereby is increased the local concentration of medicine, and whereby the patient is exempted from the general side effect caused by medicine overdose.

Another objective of the present invention is to provide a magnetic nanocomposite for inhibiting/treating cancer and a method for fabricating the same, which relates to a superparamagnetic anti-brain tumor nano drug—SPAnH/MNPs/BCNU (Superparamagnetic PAn (polyaniline)-RCOOH)/Magnetic NanoParticles/[1,3-Bis(2-chloroethyl)-1nitrosourea]) that has a high thermal stability and a low hydrolysis rate, and that can uniformly dissolve in water and thus outperforms the conventional crude anti-brain tumor medicine—BCNU having a low solubility in water, wherefore is greatly reduced the risk or side effect of injecting the anti-brain tumor medicine.

To achieve the abovementioned objectives, the present invention proposes a magnetic nanocomposite SPAnH/MNPs/BCNU, which uses a ferric ferrous oxide particle as the core and has a shell made of a carboxy-functionalized polyaniline, and which has an anti-tumor medicine bound to the shell. The magnetic nanocomposite of the present invention is particularly effective in inhibiting and treating brain tumors. The present invention improves the thermal stability of the anti-brain tumor medicine BCNU and prolongs the half life thereof from 12 hours to 30 hours at a temperature of 37° C. The half life of SPAnH/MNPs/BCNU is 36 hours when it is stored at a temperature 25° C. The half life of SPAnH/MNPs/BCNU is 33 days when it is stored at a temperature 4° C. After having been stored for 30 days, only 22% of crude BCNU remains. However, as high as 54% of the magnetic nanocomposite SPAnH/MNPs/BCNU of the present invention remains. Therefore, the medicine of the present invention obviously outperforms the conventional crude BCNU in storage stability. Further, the medicine of the present invention can uniformly dissolve in water, wherefore is overcome the problem that this type of anti-tumor medicine has low solubility in water. Moreover, the magnetic nanocomposite of the present invention has superparamagnetism, whereby the medicine can be guided to a special region to increase the local concentration of the medicine and realize a localized chemotherapy. From in-vitro cytotoxicity tests, it is known: When an 800 Gauss magnetic field is applied to 100 μM effective concentration of BCNU, the medicine of the present invention has higher killing rates in mouse malignant glioma cells and human malignant glioma cells than the conventional crude BCNU by 35% and 22%. Thus, the present invention has competitiveness in economic efficiency.

The embodiments are described in detail in cooperation with the drawings to make easily understood the objectives, characteristics and efficacies of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
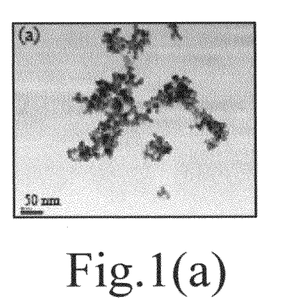
FIG. 1(a) and FIG. 1(b) are respectively TEM photographs of MNPs of Embodiment I and SPAnH/MNPs of Embodiment II.
Figure 2:
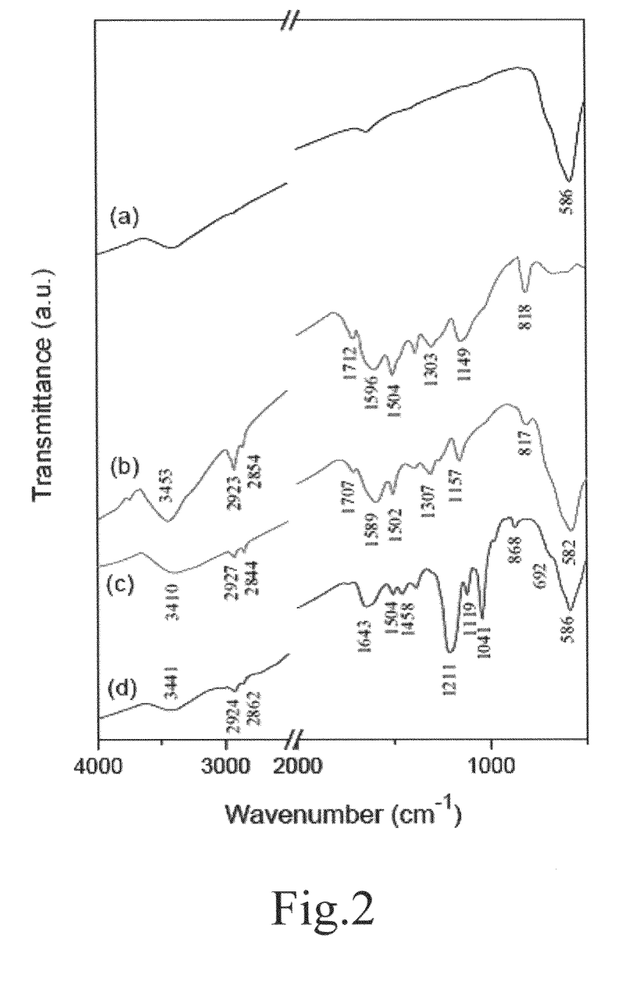
FIG. 2 is a diagram showing the infrared spectra of MNP, SPAnH, MNP/SPAnH, and SPAnH/MNPs/BCNU in Embodiments I, II and VI, wherein Curves (a)-(d) are respectively spectra of MNP, SPAnH, MNP/SPAnH, and SPAnH/MNPs/BCNU.
Figure 3:
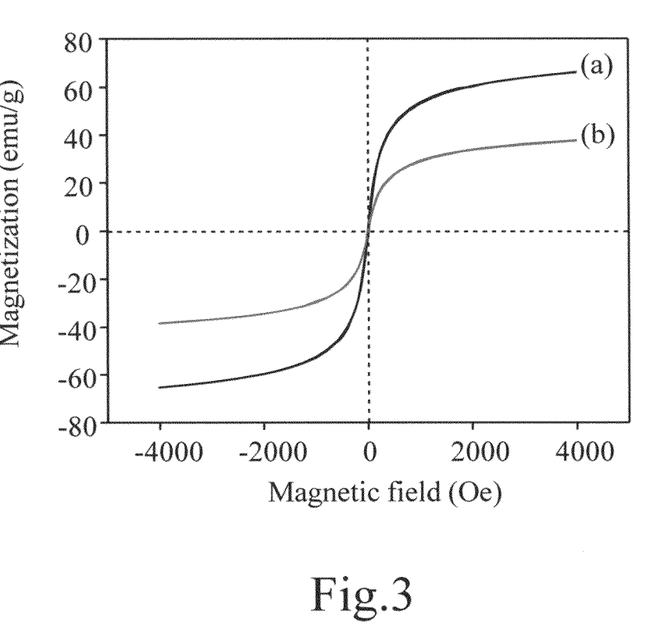
FIG. 3 is a diagram showing the magnetic hysteresis curves of MNPs and SPAnH/MNPs at an ambient temperature in Embodiments I and II, wherein Curves (a) and (b) are respectively the magnetic hysteresis curves of MNPs and SPAnH/MNPs.

Embodiment I: The Fabrication and Analysis of the Magnetic Nanoparticle of the Present Invention In this embodiment, a co-deposition method is used to fabricate the magnetic nanoparticles (MNPs) of ferric ferrous oxide ($Fe_3O_4$). Firstly, 0.7 g ($4.32 \times 10^{-3}$ mole) $FeCl_3$, 1.07 g ($6.48 \times 10^{-3}$ mole) $FeCl_2 \cdot 4H_2O$ and 400 ml of double distilled water are added into a three-necked bottle and agitated for 5 minutes at an ambient temperature to completely dissolve $FeCl_3$ and $FeCl_2 \cdot 4H_2O$. Next, 20 mL of 0.864N NaOH aqueous solution is added into the three-necked bottle, and the temperature of the solution is raised to 80° C., whereby MNPs are formed. Next, the reaction products are cooled down and vibrated with an ultrasonic vibrator to uniformly disperse the magnetic nanoparticles in the aqueous solution. Next, the mixture solution is poured into a separating funnel, and a strong magnet is placed outside the funnel to attract the magnetic nanoparticles with the solution flowing away from the bottom of the funnel, whereby the solution and the magnetic nanoparticles are separated. Next, double distilled water is used to flush the magnetic nanoparticles repeatedly until the solution is neutralized and colorless. From the TEM photograph in FIG. 1(a), it is observed that the MNPs have a particle size of about 8 nm. Curve (a) in FIG. 2 is an infrared spectrum of MNPs. The Fe—O ($v_{Fe-O}$) stretching vibration of MNPs appears at 586 cm$^{-1}$. Via SQUID (Superconducting Quantum Interference Device), the saturation magnetization of MNPs is found to be 66.2 emu/g. As shown in Curve (a) of FIG. 3, the saturation magnetization of MNPs increases with the magnetic field, and the magnetization curve passes through the origin, wherefore the MNPs of the present invention has the feature of superparamagnetism.

Figure 1B:
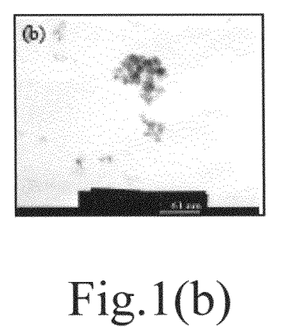

Embodiment II: The Fabrication and Analysis of the Basal Body of the Magnetic Nanocomposite of the Present Invention Firstly, 10 ml of MNPs aqueous solution having a concentration of 6.4 mg/mL and an SPAnNa (poly[aniline-co-sodium N-(1-one-butyric acid) aniline]) aqueous solution having a concentration of 4.9 mg/mL are mixed uniformly. The mixed solution is vibrated with an ultrasonic vibrator, and a 0.5M HCl solution is dropped into the mixed solution. In an acidic environment, SPAnNa aggregates and envelops magnetic nanoparticles to form basal bodies of the magnetic nanocomposite with the core being MNPs and the shell being SPAnH. Next, the basal bodies of the magnetic nanocomposite are separated from the solution and then dispersed in double distilled water. Thus are formed the SPAnH/MNPs basal bodies of the magnetic nanocomposite. From the TEM photograph in FIG. 1(b), it is observed that the SPAnH/MNPs basal bodies have a particle size of about 18 nm. Curve (b) and Curve (c) in FIG. 2 are respectively an infrared spectrum of SPAnH and an infrared spectrum of the SPAnH/MNPs basal bodies of the magnetic nanocomposite. In the infrared spectrum of the SPAnH/MNPs basal bodies, there is also a Fe—O ($v_{Fe-O}$) stretching vibration appearing at 582 cm$^{-1}$; there are a saturation-symmetric stretching vibration and a saturation-asymmetric stretching vibration of C—H ($v_{C-H}$) respectively appearing at 2844 cm$^{-1}$ and 2927 cm$^{-1}$; and there are a C=O ($v_{C=O}$) stretching vibration and an O—H ($v_{O-H}$) stretching vibration of the functional group —COOH respectively appearing at 1797 cm$^{-1}$ and 3410 cm$^{-1}$. The abovementioned stretching vibrations indicate that MNPs is indeed enveloped by a layer of SPAnH. From the SQUID measurement shown in Curve (b) of FIG. 3, it is found that the magnetic nanocomposite of the present invention has superparamagnetism with a saturation magnetization of 37.6 emu/g.

Figure 4:
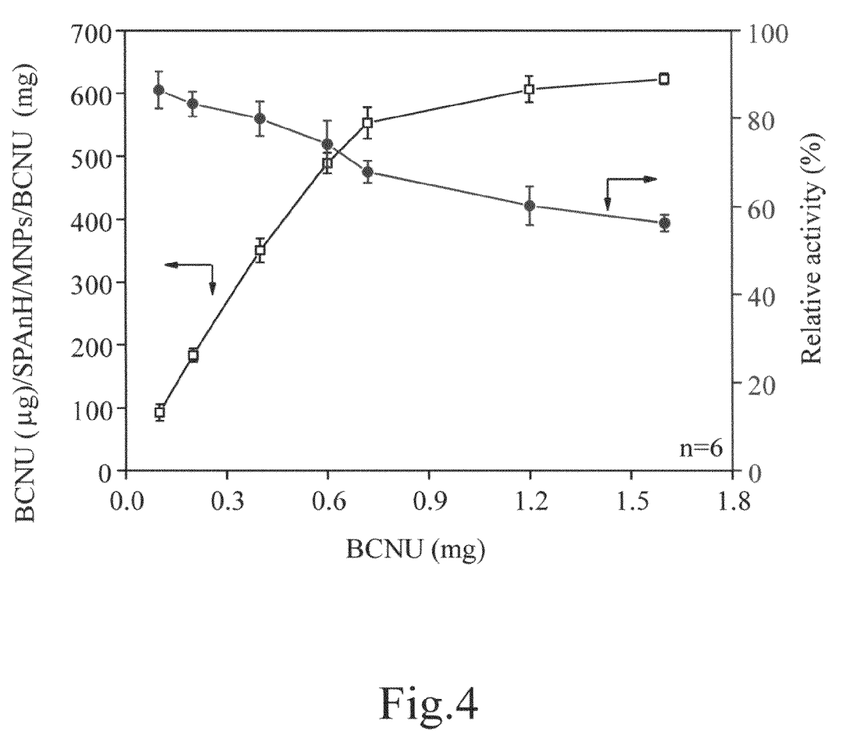
FIG. 4 is a diagram showing the quantities of bound BCNU and the activities of SPAnH/MNPs/BCNU in Embodiment IV-IX.

Embodiments III-IX: The Fabrication and Analysis of the Magnetic Nanocomposite of the Present Invention Embodiment III Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with MES buffer. Next, add 100 μg of BCNU to the product to undertake a bonding reaction at a reaction temperature of 15-20° C. for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 92.87 μg, and the activity of SPAnH/MNPs/BCNU is 86.47%.

Embodiment IV

Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with 0.1M MES buffer. Next, add 200 μg of BCNU to the product to undertake a bonding reaction for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 183.47 μg, and the activity of SPAnH/MNPs/BCNU is 83.34%.

Embodiment V

Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with 0.1M MES buffer. Next, add 400 μg of BCNU to the product to undertake a bonding reaction for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 350.89 μg, and the activity of SPAnH/MNPs/BCNU is 79.98%.

Embodiment VI

Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with 0.1M MES buffer. Next, add 600 μg of BCNU to the product to undertake a bonding reaction for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 489.3 μg, and the activity of SPAnH/MNPs/BCNU is 74.23%. Refer to Curve (d) in FIG. 2 the infrared spectrum of SPAnH/MNPs/BCNU. In Curve 2(d), there is also a Fe—O ($v_{Fe-O}$) stretching vibration appearing at 586 cm$^{-1}$; there are a saturation-symmetric stretching vibration and a saturation-asymmetric stretching vibration of C—H ($v_{C-H}$) respectively appearing at 2862 cm$^{-1}$ and 2924 cm$^{-1}$; and there are a C=O ($v_{C=O}$) stretching vibration, a C—N ($v_{C-N}$) stretching vibration of C—C—N, a N—N ($v_{N-O}$) stretching vibration of N—NO, a N=O ($v_{N=O}$) stretching vibration of N—NO and a C—Cl ($v_{C-Cl}$) stretching vibration of C—C—Cl respectively appearing at 1643 cm$^{-1}$, 1211 cm$^{-1}$, 1041 cm$^{-1}$, 1458 cm$^{-1}$ and 692 cm$^{-1}$. The abovementioned stretching vibrations indicate that SPAnH/MNPs are indeed bound to BCNU.

Embodiment VII

Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with 0.1M MES buffer. Next, add 720 μg of BCNU to the product to undertake a bonding reaction for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 552.46 μg, and the activity of SPAnH/MNPs/BCNU is 67.93%.

Embodiment VIII

Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with 0.1M MES buffer. Next, add 1200 μg of BCNU to the product to undertake a bonding reaction for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 606.38 μg, and the activity of SPAnH/MNPs/BCNU is 60.24%.

Embodiment IX

Dissolve 24 mg of EDC (1-ethyl-3-(3-dimethylaminepropyl) carbodiimide hydrochloride) and 12 mg of sulfo-NHS (N-hydroxysulfosuccinimide sodium salt) in 0.5M MES buffer (2-Morpholinoethanesulfonic acid, pH=6.3). Next, take 0.2 mL of the solution to react with 0.2 mL of SPAn/MNPs for 30 minutes and then flush the product with 0.1M MES buffer. Next, add 1600 μg of BCNU to the product to undertake a bonding reaction for 2 hours. Next, flush off free BCNU with ethyl alcohol and deionized water. Determine the quantity of the flushed-off free BCNU with HPLC (High Performance Liquid Chromatography) under the conditions of using a solution of alcohol/water (v/v) 60/40, a flow rate of 2 mL/min and a detected wavelength of 270 nm. Work out the quantity of BCNU bound to SPAnH/MNPs from the quantity of the free BCNU. As shown in FIG. 4, the quantity of BCNU bound to SPAnH/MNPs is 622.94 μg, and the activity of SPAnH/MNPs/BCNU is 56.32%.

The above-mentioned Embodiments III-IX, N-Ethyl-N'-(3-dimethylaminopropyl)carbodiimide (EDC) or N,N'-Dicyclohexylcarbodiimide (DCC) and N-hydroxysuccinimide (NHS) or N-Hydroxysulfosuccinimide sodium salt (sulfo- NHS) are used to enable a bonding reaction between the anti-brain tumor medicine and the basal body of the magnetic nanocomposite.

Figure 5:
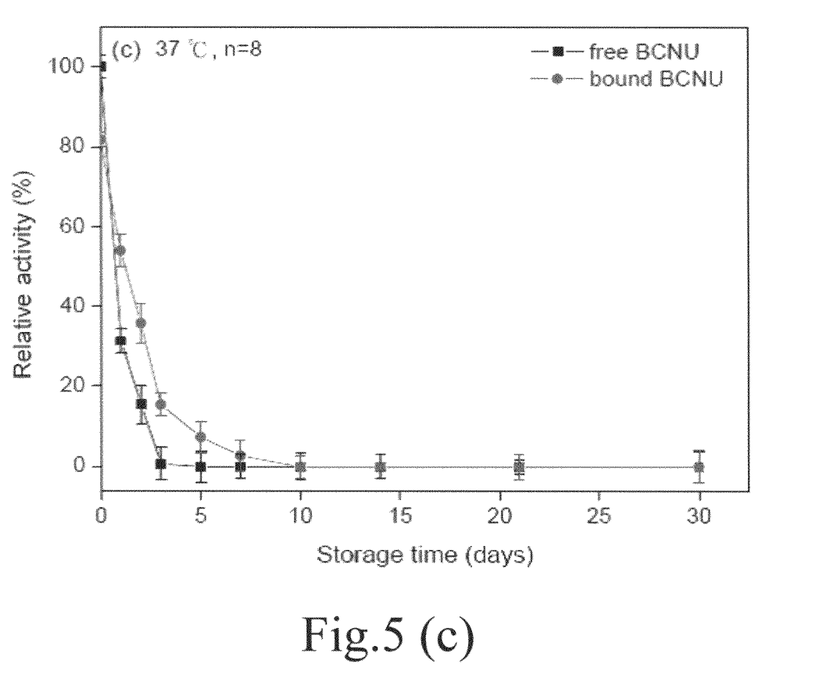
FIGS. 5(a)-5(c) are diagrams showing the curves of storage stability of crude BCNU and SPAnH/MNPs/BCNU respectively stored at temperatures of 4° C., 25° C. and 37° C. in Embodiment X.
Figure 5A:
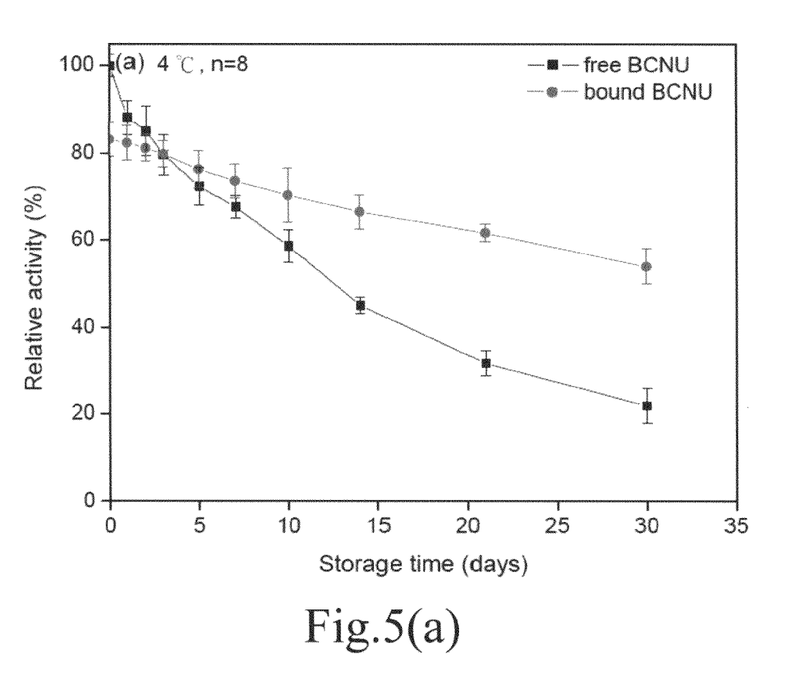
Figure 5B:
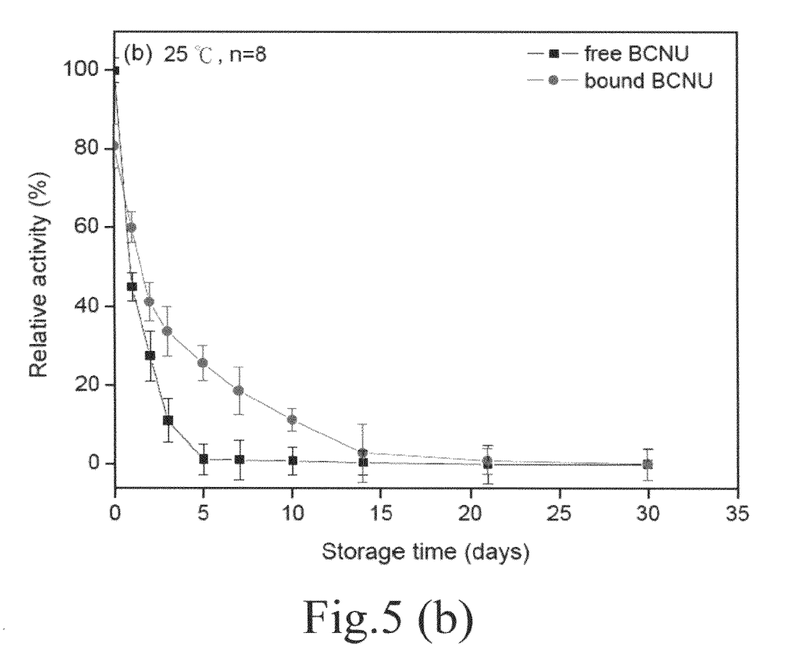

Embodiment X: The Analysis of the Storage Stability of the Magnetic Nanocomposite of the Present Invention Store the conventional crude BCNU and the magnetic nanocomposite (SPAnH/MNPs/BCNU) of the present invention respectively at temperatures of 4° C., 25° C. and 37° C. Use the Bratton-Marshall assay to detect the residual activities after the storages of 1-30 days for comparing the storage stabilities. Refer to FIGS. 5(a)-5(c). In the case of storing at 4° C., the conventional crude BCNU has a half life of 12.5 days, and SPAnH/MNPs/BCNU has a half life of 33 days. In the case of storing at 25° C., the conventional crude BCNU has a half life of 22 hours, and SPAnH/MNPs/BCNU has a half life of 36 hours. In the case of storing at 37° C., the conventional crude BCNU has a half life of 12 hours, and SPAnH/MNPs/BCNU has a half life of 30 hours. It proves that SPAnH/MNPs/BCNU has a lower hydrolysis rate and a higher stability than the conventional crude BCNU.

Figure 6:
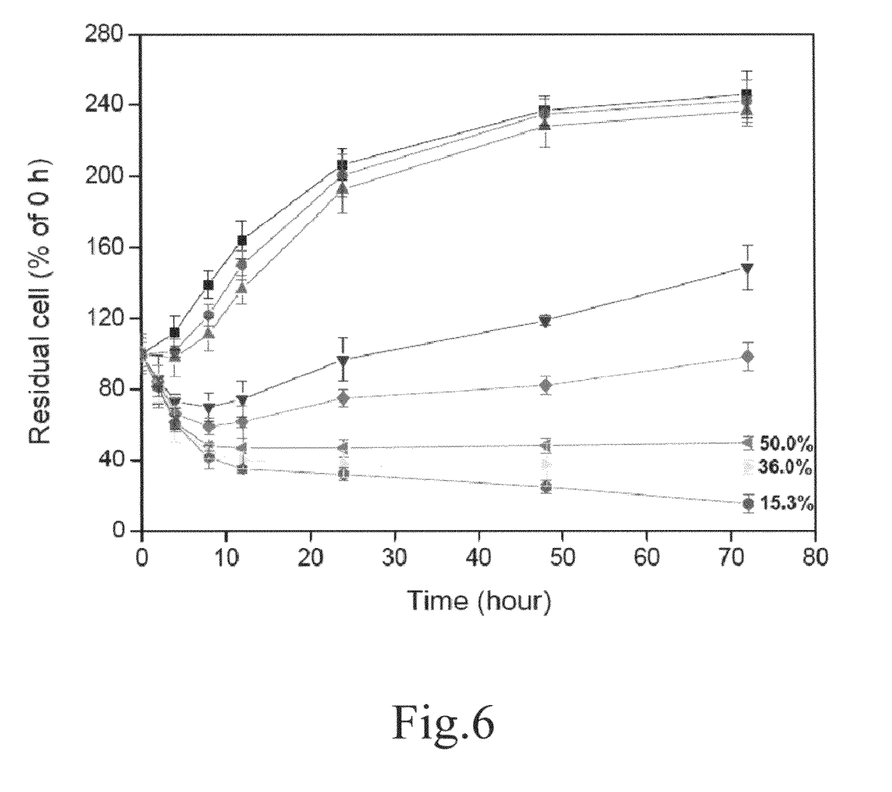
FIG. 6 is a diagram showing the growth curves of C6 cells in Embodiment XI, wherein the 72-hour cell growth curves are from top to bottom respectively of the cases: the control group, SPAnH/MNPs, SPAnH/MNPs under an 800 Gauss magnetic field, BCNU having an effective concentration of 20 μM, BCNU having an effective concentration of 50 μM, crude BCNU having an effective concentration of 100 μM, BCNU having an effective concentration of 100 μM, BCNU having an effective concentration of 100 μM and under an 800 Gauss magnetic field.

Embodiments XI-XV: The In Vitro Toxicity Test and the In Vitro Cancer Cell Killing Rate Test of the Magnetic Nanocomposite of the Present Invention Embodiment XI Place 150 μL of a mixture liquid containing 10000 mouse glioma cells (C6) into every well of a 96-well culture plate. Place the culture plates in a humidified incubator at a temperature of 37 C.° and with 5% $CO_2$ to enable adherent growth of the cells. 24 hours later, add to the wells 50 μL of MNP (600 μg/mL), BCNU or SPAnH/MNPs/BCNU dispersed in the RPMI1640 medium. MNP, BCNU and SPAnH/MNPs/BCNU respectively have final concentrations of 20, 50 and 100 μM in the wells. After the addition of MNP, BCNU and SPAnH/MNPs/BCNU, observe the growth of the cells 8, 12, 24, 48 and 72 hours later. Once cell counting begins, remove RPMI1640 and add 120 μL of an XTT reaction liquid (2,3-Bis(2-methoxy-4-nitro-5-sulfophenyl)-2H-tetrazolium-5-carboxanili de inner salt). Use an ELISA reader (BIO-TEK, model EL 808) to measure the OD value at 499 nm to estimate the toxicity of SPAnH/MNPs and the cell-killing rate of SPAnH/MNPs/BCNU. Refer to FIG. 6 for the results. SPAnH/MNPs do not show any toxicity to C6 cells after the C6 cells have been cultivated together with SPAnH/MNPs for 72 hours. Even when a magnetic field is applied to move SPAnH/MNPs to the C6 cells, C6 cells are not poisoned by SPAnH/MNPs either. In the cases that 20 μM and 50 μM of SPAnH/MNPs/BCNU are added, the C6 cell growth-inhibition ratios are respectively 30% and 40% 8 hours later. However, division and growth of C6 cells still occurs 8 hours later because the concentrations of medicine are unlikely to kill all the cells. In the cases that 100 μM of BCNU and SPAnH/MNPs/BCNU are added, the C6 cell growth-inhibition ratios are respectively 53% and 60% 12 hours later, and the inhibiting effect can persist for 72 hours. In the cases that an 800 Gauss magnetic field is applied to the culture plates, the C6 cell growth-inhibition ratio increases to as high as 85%. The magnetic field can guide SPAnH/MNPs/BCNU to concentrate around C6 cells. Thus, the cells are fed with more medicine and poisoned more seriously.

Embodiment XII

Figure 7:
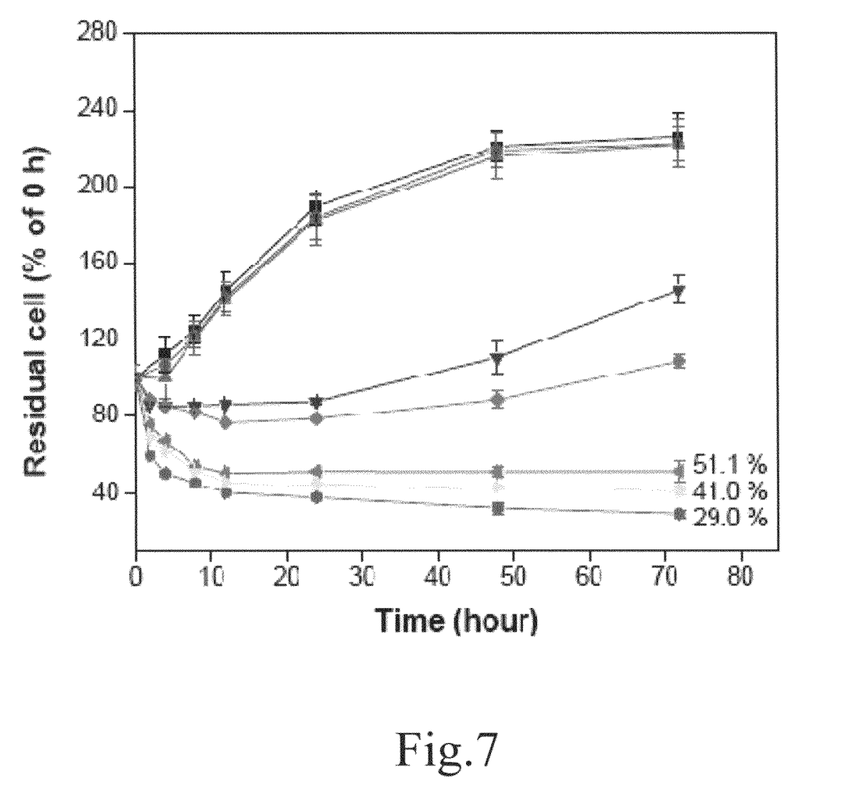
FIG. 7 is a diagram showing the growth curves of U87 cells in Embodiment XII, wherein the 72-hour cell growth curves are from top to bottom respectively of the cases: the control group, SPAnH/MNPs, SPAnH/MNPs under an 800 Gauss magnetic field, BCNU having an effective concentration of 20 μM, BCNU having an effective concentration of 50 μM, crude BCNU having an effective concentration of 100 μM, BCNU having an effective concentration of 100 μM, BCNU having an effective concentration of 100 μM and under an 800 Gauss magnetic field.
Figure 8A:
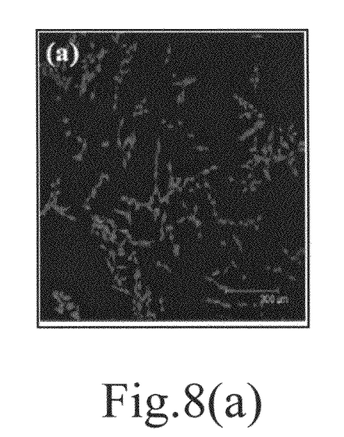
FIGS. 8(a)-8(d) are the fluorescent images of the cases: C6 cells are cultivated together with SPAnH/MNPs (150 m/mL) for 1 day, 2 days, 4 days and 6 days in Embodiment XIII.
Figure 8B:
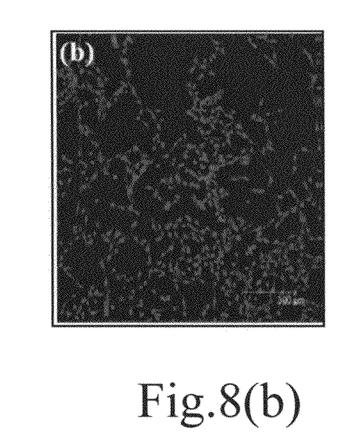
Figure 8C:
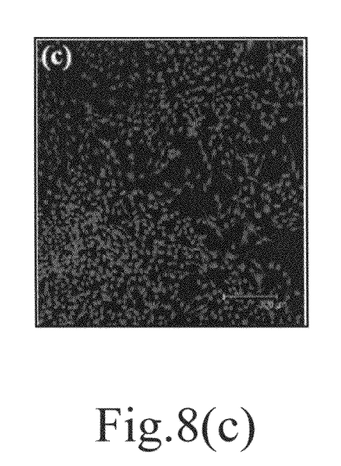
Figure 8D:
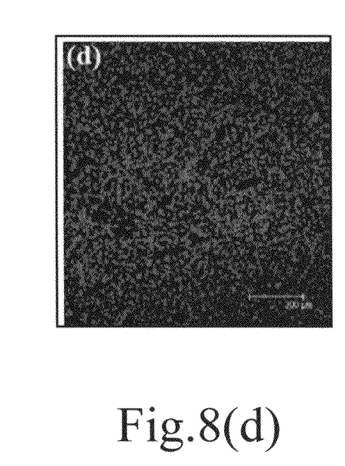
Figure 9A:
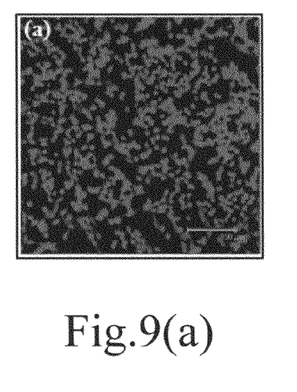
FIGS. 9(a)-9(e) are the fluorescent images of the cases: C6 cells are cultivated for 8 hours together with SPAnH/MNPs, 20 μM SPAnH/MNPs/BCNU, 100 μM crude BCNU, 100 μM SPAnH/MNPs/BCNU, and 100 μM SPAnH/MNPs/BCNU under a magnetic field.
Figure 9B:
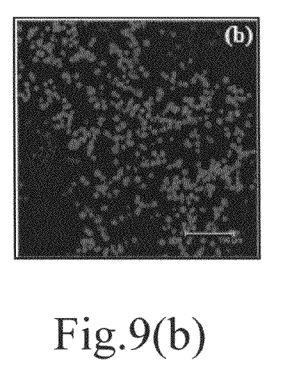
Figure 9C:
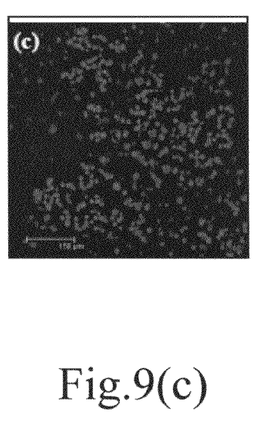
Figure 9D:
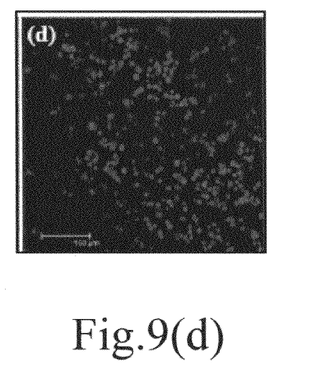
Figure 9E:
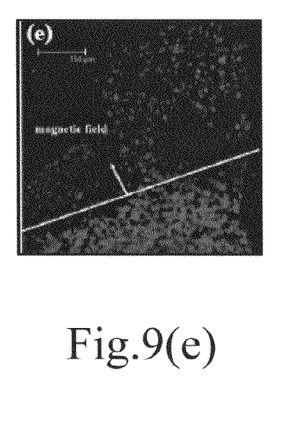

Place 150 μL of a mixture liquid containing 10000 human glioma cells (U87) into every well of a 96-well culture plate. Place the culture plates in a humidified incubator at a temperature of 37 C.° and with 5% $CO_2$ to enable adherent growth of the cells. 24 hours later, add to the wells 50 μL of MNP (600 μg/mL), BCNU or SPAnH/MNPs/BCNU dispersed in the RPMI1640 medium. MNP, BCNU and SPAnH/MNPs/BCNU respectively have final concentrations of 20, 50 and 100 μM in the wells. After the addition of MNP, BCNU and SPAnH/MNPs/BCNU, observe the growth of the cells 8, 12, 24, 48 and 72 hours later. Once cell counting begins, remove RPMI1640 and add 120 μL of an XTT reaction liquid (2,3-Bis(2-methoxy-4-nitro-5-sulfophenyl)-2H-tetrazolium-5-carboxanili de inner salt). Use an ELISA reader (BIO-TEK, model EL 808) to measure the OD value at 499 nm to estimate the toxicity of SPAnH/MNPs and the cell-killing rate of SPAnH/MNPs/BCNU. Refer to FIG. 7 for the results. SPAnH/MNPs do not show any toxicity to U87 cells after the U87 cells have been cultivated together with SPAnH/MNPs for 72 hours. Even when a magnetic field is applied to move SPAnH/MNPs to the U87 cells, U87 cells are not poisoned by SPAnH/MNPs either. In the cases that 20 μM and 50 μM of SPAnH/MNPs/BCNU are added, the U87 cell growth-inhibition ratios are respectively 14% and 18% 8 hours later. However, division and growth of U87 cells still occurs 8 hours later because the concentrations of medicine are unlikely to kill all the cells. In the cases that 100 μM of BCNU and SPAnH/MNPs/BCNU are added, the U87 cell growth-inhibition ratios are respectively 49% and 59% 72 hours later, and the inhibiting effect persists. In the cases that an 800 Gauss magnetic field is applied to the culture plates, the U87 cell growth-inhibition ratio increases to as high as 71%. The magnetic field can guide SPAnH/MNPs/BCNU to concentrate around U87 cells. Thus, the cells are fed with more medicine and poisoned more seriously.

Embodiment XIII

Apply 2 mL of a mixture liquid containing 1% gelatin and 20000 C6 cells onto 3.5 cm-diameter dishes. Place the dishes in a humidified incubator at a temperature of 37 C.° and with 5% $CO_2$ to enable adherent growth of the cells. 24 hours later, add to the dishes 100 μL of a mixture solution where SPAnH/MNPs are dispersed in the RPMI1640 medium. In the first, second, fourth and sixth days from the addition, flush the contents of the dishes with 1 mL of HBSS (Hanks' Balance Slat Solution). FIGS. 8(a)-8(d) show the fluorescent images of the C6 cells that have been cultivated together with SPAnH/MNPs (150 μg/mL) for 1-6 days. From FIGS. 8(a)-8(d), it is found that the cells (green fluorescence) increase with the time of cultivation. It indicates that MNP/SPAnH is non-toxic to C6 cells. Such a result matches the growth curve of the cells.

Embodiment XIV

Apply 2 mL of a mixture liquid containing 1% gelatin and 20000 C6 cells onto 3.5 cm-diameter dishes. Place the dishes in a humidified incubator at a temperature of 37 C.° and with 5% $CO_2$ to enable adherent growth of the cells. 24 hours later, add to the dishes 100 μL of SPAnH/MNPs, 100 μM BCNU, 20 μM SPAnH/MNPs/BCNU or 100 μM SPAnH/MNPs/BCNU dispersed in the RPMI1640 medium. 8 hours later from the addition, flush the contents of the dishes with 1 mL of HBSS (Hanks' Balance Slat Solution). FIGS. 9(a)-9(e) show the fluorescent images of the C6 cells. From FIGS. 9(a)-9(e), find that the dead cells (red fluorescence) increase with the concentration of SPAnH/MNPs/BCNU, and that 100 μM SPAnH/MNPs/BCNU kills more cells than 100 μM BCNU. Such a result matches the growth curve of cells. When a magnetic field is applied to a specified area (the area above the white line in FIG. 9(e)), most SPAnH/MNPs/BCNU is attracted to the specified area. Thus, cells are massively killed in the specified area. A great amount of green fluorescence, which represents live cells, appears in the area where SPAnH/MNPs/BCNU is impoverished. The results show that a magnetic field can guide SPAnH/MNPs/BCNU to a special area to increase the local concentration of medicine.

Embodiment XV

Figure 1C:
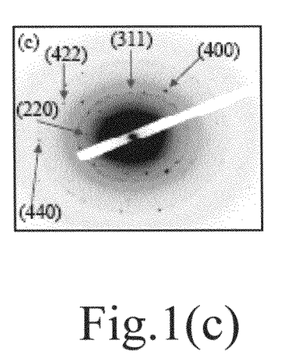
FIG. 1(c) is a TEM electron diffraction pattern of SPAnH/MNPs in Embodiment XV.
Figure 1D:
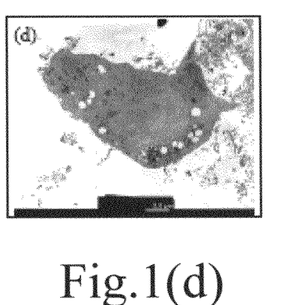
FIG. 1(d) and FIG. 1(e) are respectively 3000× and 10000× TEM photographs of C6 cells in Embodiment XV.
Figure 1E:
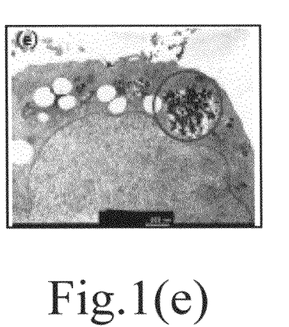
Figure 1F:
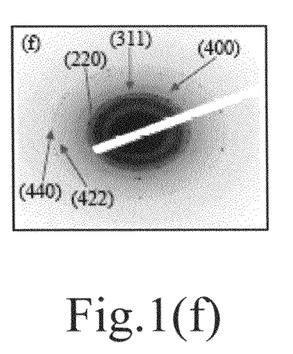
FIG. 1(f) is a TEM electron diffraction pattern of SPAnH/MNPs inside the circle in FIG. 1(e)
Figure 1G:
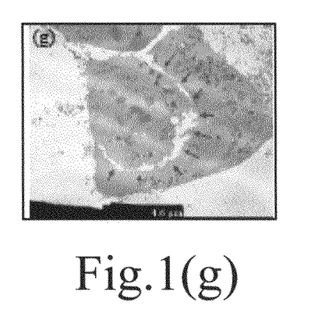
FIG. 1(g) and FIG. 1(h) are respectively 2000× and 5000× TEM photographs showing that bound BCNU enters C6 cells in Embodiment XV.
Figure 1H:
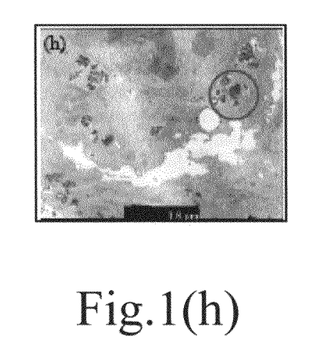
Figure 1I:
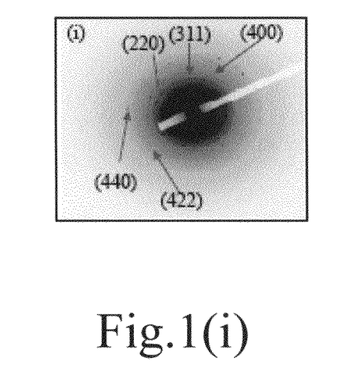
FIG. 1(i) is a TEM electron diffraction pattern of the bound BCNU in FIG. 1(h)

Respectively cultivate C6 cells together with SPAnH/MNPs and SPAnH/MNPs/BCNU for 8 hours. Slice the samples. Use TEM (Transmission Electron Microscope) to observe the diameter of MNPs and the distribution of the cells, and use electron diffraction pattern to detect the crystallographic structures. From FIG. 1(c), it is known that the diameters of MNPs and SPAnH/MNPs are respectively 8 nm and 18 nm. From the electron diffraction analysis, it is found that the crystallographic planes are respectively (400), (311), (422), (220) and (440). It can prove that MNPs and SPAnH/MNPs contain $Fe_3O_4$ crystal according to JCPDS (Joint Committee on Powder Diffraction Standards). From FIG. 1(d) and FIG. 1(e), it is known that SPAnH/MNPs can enter the cells via pinocytosis. From the electron diffraction pattern in FIG. 1(f), it is known that the crystallographic planes of the black particles inside the circle in FIG. 1(e) are respectively (400), (311), (422), (220) and (440), which are identical to those of MNPs. It can prove that the particles inside the cell are SPAnH/MNPs. In the case that SPAnH/MNPs/BCNU is added to the culture dishes containing C6 cells, it is found: After 8 hours of cultivation, the bound BCNU enters the cells via pinocytosis and performs the anti-cancer function to peel off the cell nucleus and cause the death of the cell, as shown in FIG. 1(g) and FIG. 1(h). FIG. 1(i) proves that the black particles entering the cell also contain MNPs. The above-mentioned results show that the SPAnH/MNPs composite can indeed enter the cell and that SPAnH/MNPs can carry BCNU into the cell.

Figure 10:
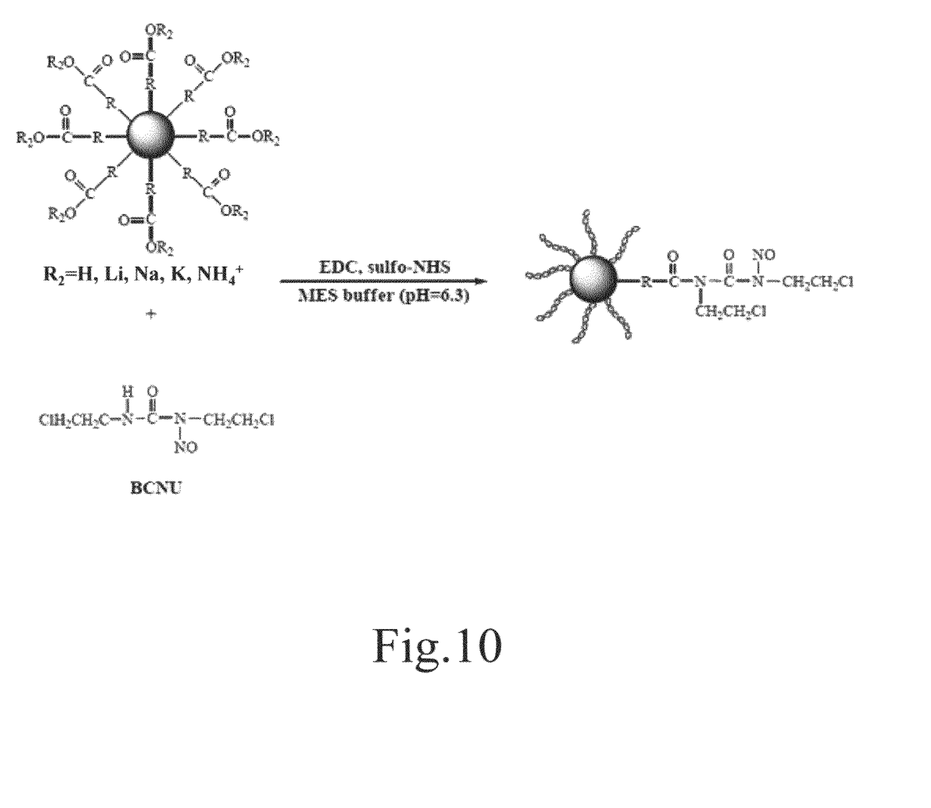
FIG. 10 is a diagram schematically showing the chemical reaction that the anti-cancer medicine BCNU is bound to the magnetic nanocomposite SPAnH/MNPs in Embodiments III-IX.

The anti-malignant glioma magnetic nanocomposite (SPAnH/MNPs/BCNU) of the present invention has been demonstrated in the embodiments described above. In summary, the medicine of the present invention uses a basal body of a magnetic nanocomposite as the vector. The magnetic nanocomposite of the present invention adopts magnetic ferric ferrous oxide nanoparticle as the core and adopts a carboxy-functionalized polyaniline as the shell. The anti-brain tumor medicine BCNU (1,3-bis(2-chloroethyl)-1-nitrosourea, Carmustine) is bound to the outer surface of the shell by covalent bonds. FIG. 10 shows the chemical reaction of forming the medicine of the present invention. The magnetic nanocomposite (SPAnH/MNPs/BCNU) of the present invention outperforms the conventional crude BCNU in stability and anti-hydrolysis capability. Further, the magnetic nanocomposite medicine of the present invention can be guided to a special area to increase the local concentration and realize a local chemotherapy. Therefore, the present invention has competitive advantage over the conventional BCNU.

In conclusion, the present invention can fast fabricate a magnetic nanocomposite containing multiple bioreactive functional groups in a simple way without using any of toxic chemicals, such as active agents, dispersants and cross-linking agents. The present invention anchors the anti-tumor medicine to the surface of the magnetic nanocomposite to lower the hydrolysis rate of the medicine. Further, the present invention can disperse the water-insoluble medicine in water uniformly to decrease the biological rejection. Furthermore, the magnetic nanocomposite unit of the present invention has a large surface area to anchor a great number of medicine molecules. Moreover, the magnetic nanocomposite of the present invention has superparamagnetism and can be rapidly guided to the nidus by an external magnetic field to increase the local concentration of the medicine and provide an effective chemotherapy.

In the present invention, the magnetic nanocomposite has a diameter of 25-50 nm; the magnetic nanoparticle has an average diameter of 5-100 nm; the core of the magnetic nanocomposite is selected from the nanoparticles of $Fe_3O_4$, $Fe_2O_3$, and Ni; the shell of the magnetic nanocomposite is made of a carboxy-functionalized polyaniline, wherein the carboxy-functionalized polyaniline contains carboxyl groups bonded to side chains of a polyaniline and has the following structural formula:

wherein R is selected from a group consisting of, —$COR_1COOH$, —$COR_1COO^-$, —$COR_1COOLi$, —$COR_1COONa$, —$COR_1COOK$, and —$COR_1COONH_4^+$, and wherein $R_1$ is selected from a group consisting of $C_2$-$C_4$ alkyl groups and $C_2$-$C_4$ alkenyl groups, and wherein m, x and y are integers respectively within 3-2000, 0-1, and 0-1.

In the present invention, the anti-tumor medicine bound to the magnetic nanocomposite is a carboxy-functionalized medicine and may be selected from a group consisting of BCNU (1,3-bis(2-chloroethyl)-1-nitrosourea), CCNU (N-(2-chloroethyl)-N'-cyclohexyl-N— nitrosourea), MCNU (methyl 6-(3-(2-chloroethyl)-3-nitrosoureido), Cl-ENU ((2-chloroethyl)nitrosourea), HO-ENU (N-(2-hydroxyethyl)-N-nitrosoure) and MNU (1-methyl-1-nitrosourea).

The embodiments described above are only to exemplify the present invention but not to limit the scope of the present invention. Any equivalent modification or variation according to the spirit of the present invention is to be also included within the scope of the present invention, which is based on the claims stated below.

What is claimed is:

1. A magnetic nanocomposite for inhibiting and treating cancer, comprising
   a core formed of a plurality of magnetic nanoparticles made of ferric ferrous oxide ($Fe_3O_4$);
   a shell made of a carboxy-functionalized polyaniline and enveloping said core,
   wherein said carboxy-functionalized polyaniline contains carboxyl groups bonded to side chains of a polyaniline and has a structural formula:

wherein R is selected from a group consisting of —$COR_1COOH$, —$COR_1COO^-$, —$COR_1COOLi$, —$COR_1COONa$, —$COR_1COOK$, and —$COR_1COONH_4^+$, and wherein $R_1$ is selected from a group consisting of $C_2$-$C_4$ alkyl groups and $C_2$-$C_4$ alkenyl groups, and wherein m, x and y are integers respectively within 3-2000, 0-1, and 0-1;

wherein an anti-tumor medicine is bound to said carboxyl groups of said shell, said anti-tumor medicine is BCNU (1,3-bis(2-chloroethyl)-1-nitrosourea,Carmustine):and the concentration of said BCNU in said maimetic nanocomposite is 37.5 wt %.

2. The magnetic nanocomposite for inhibiting and treating cancer according to claim 1, wherein said anti-tumor medicine is bound to said external surface of said shell via covalent bonds.

3. The magnetic nanocomposite for inhibiting and treating cancer according to claim 1, wherein said magnetic nanoparticles have an average diameter of 5-100 nm.

4. The magnetic nanocomposite for inhibiting and treating cancer according to claim 1, wherein said core further comprises a plurality of magnetic nanoparticles made of ferric oxide ($Fe_2O_3$) or a plurality of magnetic nanoparticles made of nickel.

5. A method for fabricating a magnetic nanocomposite for inhibiting and treating cancer, comprising steps:

providing a basal body of a magnetic nanocomposite, wherein said basal body of said magnetic nanocomposite includes a core and a shell, and wherein said core is formed of a plurality of magnetic nanoparticles made of ferric ferrous oxide ($Fe_3O_4$), and wherein said shell is made of a carboxy-functionalized polyaniline and envelopes said core, wherein said carboxy-functionalized polyaniline contains carboxyl groups bonded on side chains of a polyaniline and has a structural formula:

wherein R is selected from a group consisting of —$COR_1COOH$, —$COR_1COO^{31}$, —$COR_1COOLi$, —$COR_1COONa$, —$COR_1COOK$, and —$COR_1COONH_4^+$, and wherein $R_1$ is selected from a group consisting of $C_2$-$C_4$ alkyl groups and $C_2$-$C_4$ alkenyl groups, and wherein m, x and y are integers respectively within 3-2000, 0-1, and 0-1;

attaching an anti-tumor medicine to the carboxyl groups of said shell via covalent bonds, wherein said anti-tumor medicine is BCNU (1,3-bis(2-chloroethyl)-1-nitrourea, Carmustine) and the concentration of said BCNU in said magnetic nanocomposite is 37.5 wt %; and performing a purification process with magnetic separation and flushing to obtain a magnetic nanocomposite.

6. The method for fabricating a magnetic nanocomposite for inhibiting and treating cancer according to claim 5, wherein said BCNU reacts at a specified temperature range between 15 and 20° C.

7. The method for fabricating a magnetic nanocomposite for inhibiting and treating cancer according to claim 5, wherein said BCNU reacts for a given time interval of 2 hours.

8. The method for fabricating a magnetic nanocomposite for inhibiting and treating cancer according to claim 5, wherein in said step of attaching said anti-tumor medicine, N-Ethyl-N'-(3-dimethylaminopropyl)carbodiimide (EDC) or N,N'-Dicyclohexylcarbodiimide (DCC) and N-hydroxysuccinimide (NHS) or N-Hydroxysulfosuccinimide sodium salt (sulfo-NHS) are used to enable a bonding reaction between said anti-tumor medicine and said basal body of said magnetic nanocomposite.

9. The method for fabricating a magnetic nanocomposite for inhibiting and treating cancer according to claim 5, further comprising a step of applying a magnetic field to guide said magnetic nanocomposite to cancer cells to perform a localized chemotherapy.

10. The method for fabricating a magnetic nanocomposite for inhibiting and treating cancer according to claim 5, wherein said magnetic nanocomposite has an average diameter of 25-50 nm.

11. The method for fabricating a magnetic nanocomposite for inhibiting and treating cancer according to claim 5, wherein said magnetic nanoparticles have an average diameter of 5-100 nm.

12. The method for fabricating a magnetic nanocomposite for inhibiting and treating cancer according to claim 5, wherein said core further comprises a plurality of magnetic nanoparticles made of ferric oxide ($Fe_2O_3$) or a plurality of magnetic nanoparticles made of nickel.

* * * * *